Sept. 23, 1969 R. PECOFF Plant Pat. 2,920
ACACIA PLANT
Filed Sept. 29, 1967
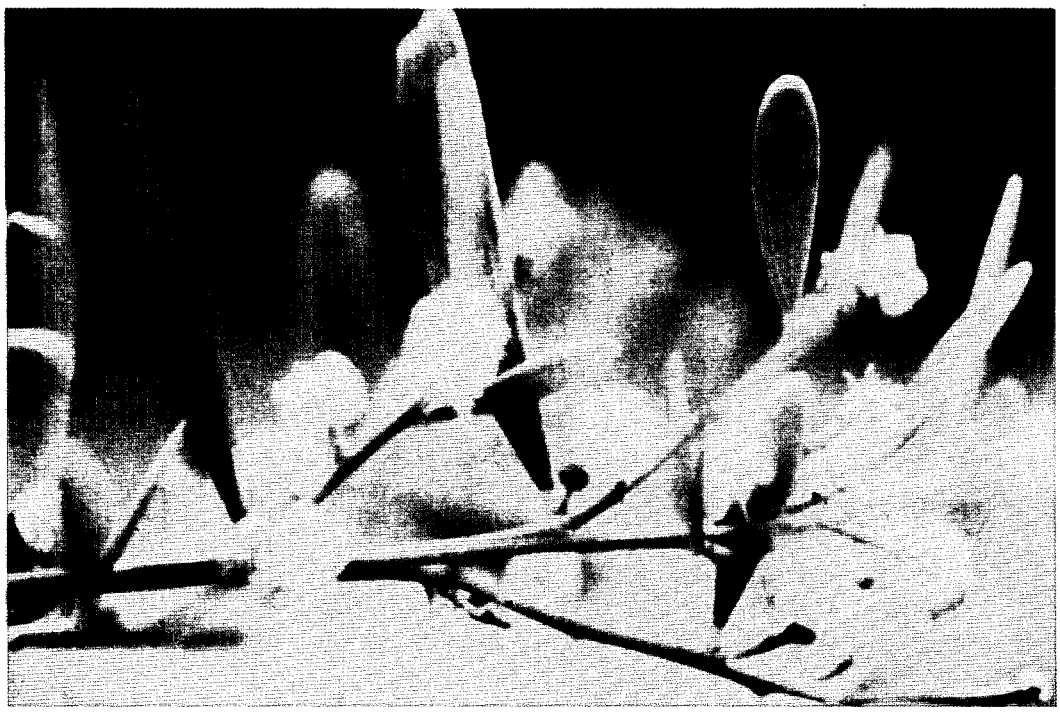
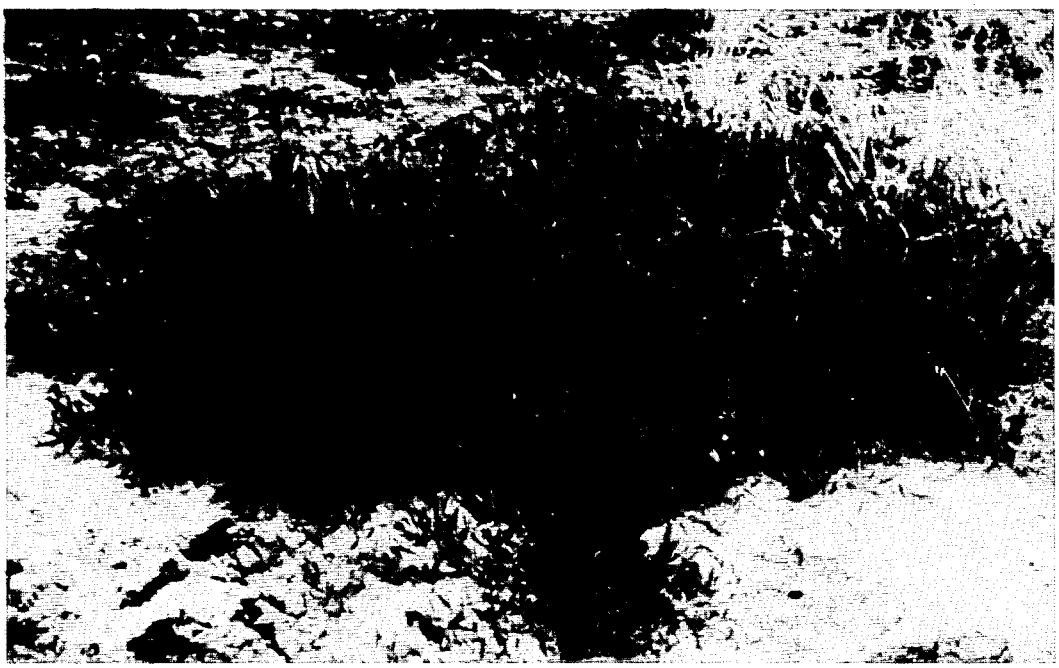
Inventor.
Ronald Pecoff
By: Robbs & Robb
Attorneys.

United States Patent Office

Plant Pat. 2,920
Patented Sept. 23, 1969

2,920
ACACIA PLANT

Ronald Pecoff, 9200 Pershing Drive,
Playa del Rey, Calif. 90291

Filed Sept. 29, 1967, Ser. No. 671,899
Int. Cl. A01h 5/00
U.S. Cl. Plt.—54 1 Claim The present invention relates to a new and distinct variety of Acacia plant which was discovered by me as a newly found seedling in a cultivated region embracing an aboriginal water hole which actually is a clay salt flat which fills with rain water during the winter months, near the village of Ongerup, in Western Australia.

At the time of my discovery I was seeking salt-tolerant plants suitable for ground cover or for general landscape use, and as I walked through the salt flat referred to in the foregoing, my attention was attracted to a prostrate, compact, spreading, silver-gray shrub having a vanilla-like fragrance and which was the only plant growing in this particular area except for Halophytes or salt marsh plants. About a distance of one mile away, I found large stands of Acacia of the species botanically known as *Acacia ixiophylla,* (classification identified in "Key to the Western Australia Wild Flowers," part I, by W. E. Blackall) growing to 12 feet high, so I believe that my newly found prostrate variety was a seed mutation of that species which usually grows very tall and forms a very large round shrub which thrives only in sandy and well-drained soils having a neutral pH, and is readily subject to attack by insects and has no fragrance.

On finding the new prostrate variety, I carefully preserved the same and took tip cuttings thereof for propagation in my nursery at Playa del Rey, Calif. Continued observations and tests of the plants derived from the aforementioned tip cuttings, as well as additional plants propagated by me in California by primary and secondary cuttings, have convinced me that I have found and developed a new and improved Acacia variety which is distinguished from its parent, as well as from all other Acacia varieties heretofore known, as evidenced by the following unique combination of characteristics, among others, which are outstanding in the view variety:

(1) A prostrate but spreading habit of growth suitable for ground cover and ideal for hillside erosion control;

(2) Distinctive and attractive Silvery Leek Green colored foilage;

(3) Profuse production of attractive yellow flowers, usually in the spring and fall seasons in California;

(4) A distinctive and pleasing vanilla-like fragrance derived from the leaves, stems and the flowers;

(5) The unusual ability to be propagated readily in a true prostrate form by cuttings;

(6) Good resistance to insects and diseases;

(7) Good weather tolerance, including good resistance to temperatures as high as 140° F. and as low as 18° F., good resistance to frost and/or occasional snow, and prolonged periods of drought (up to at least 8 months) and rainfall (up to as much as 9 to 14 inches); and (8) The ability to thrive in heavy clay soils and in coastal salt wind conditions while growing in dredged ocean soils, as well as thriving in hot interior regions, with a pH tolerance as high as 9.6.

The accompanying drawing shows typical plants of my new variety as grown in my California nursery, as well as specimens of the foilage and flowers on a somewhat enlarged scale, all as depicted in color as nearly true as it is reasonably possible to make the same in a color illustration of this character.

The following is a detailed description of my new variety, with color terminology in accordance with Wilson's Horticultural Colour Chart, published in collaboration with the Royal Horticultural Society, except where general color terms of ordinary dictionary significance are obvious:

Parentage: A seed mutation of an unnamed variety of the species botanically known as *Acacia ixiophylla.*

Propagation: Holds its distinguishing characteristics through succeeding propagations by cuttings.

Locality where grown and observed: Playa del Rey, Calif.

PLANT

Form: Low-growing (reaches height of only about 28 inches); much-branched; compact; lateral stem growth usually ranges from 12 inches to 18 inches radiating outward from center.

Habit: Vigorous; drawf; branching; compact, but spreading up to about 15 feet wide while remaining prostrate.

Rootings: Roots easily from both primary and secondary-half-ripe, thick stem cuttings and is the only Acacia which can be asexually reproduced in a true prostrate form.

Blooming habit: Flowers borne in a small globular head of from 15 to 20 flowers each, with peduncles in pairs on short racemes of 3 or 4; mostly 5-merous and consisting of 5 free sepals which are narrow-spatulate; each globular head averages about ¼ inch across when fully extended, with peduncles averaging about 5/16 inch long.

Blooming season (in California): From March through May and again from September through October.

Foliage:

*Leaves.*—Flat. Size: length—about 2¼ inches; width—about ¾ inch. Quantity—abundant. Color: new foliage— upper side—Spinach Green, Plate 0960/2; under side—Spinach Green, Plate 0960/2; old foliage—upper side—Silvery Leek Green, Plate 858/1; under side—Silvery Leek Green, Plate 858/1. Shape—from lanceolate to broadly linear, with a retuse apex that is concave and indented to form a cavity at the apex. Texture: upper side—leathery and corrugated, with a mealy pubescent powder and many fine parallel lines and ridges. underside—leathery and corrugated, with a mealy pubescent powder and many fine parallel lines and ridges. Margin—entire; smooth. Aspect—small glandular oil cells cover the entire area of the leaf, and if the stem or leaf is crushed, cells emit a vanilla-like fragrance.

*Stems.*—Color—Cobalt Violet, Plate 634/1 at upper end or top of stem when mature, quite different from parent variety, but not shown at stage depicted in drawing.

Disease and insect resistance: Has shown complete immunity to disease and insects, as determined by comparison with other varieties of Acacias grown under the same conditions at Playa del Rey, Calif., while said other varieties were attacked by borers and insects which normally spread diseases, with immunity of my new variety probably being attributed to glandular oil present in the new variety which tends to inhibit insects and spread of diseases.

FLOWER

Borne: In globules of 15 to 20 flowers on short racemes.

Color: Yellow Ochre, Plate 7/1.

FRUIT

Shape: A 2-valved pod; flexuose; glabrous; about 1½ inches long and about ⅛ inch wide.

Color of pod: Snuff brown.

Seeds: Oblong; about 3/16 inch long and 3/32 inch wide; black in color.

Fruiting season: Sets fruit in July; bloom begins in November in southern California and continues through the end of February, followed by setting of fruit.

GENERAL OBSERVATIONS

Hardiness: Resistant to cold weather as low as 180° F. and tolerant to frost and occasional snow; resistant to hot weather as high as 140° F.; withstands long periods of drought up to 8 months, as well as excessive "wet feet" or flooding in from 9 to 14 inches of rainfall.

Soil conditions: Grows well in heavy clay and wet soils and also loams, and withstands pH values as high as 9.6, unlike any other known Acacia variety; ideal for hillside erosion control.

Trimming: Can withstand severe trimming or pruning without harmful effects.

I claim:

1. A new and distinct variety of Acacia plant, substantially as herein shown and described, characterized particularly as to novelty by the unique combination of a prostrate but spreading habit of growth suitable for ground cover and ideal for hillside erosion control, distinctive and attractive Silvery Leek Green colored foliage, profuse production of attractive yellow flowers, usually in the spring and fall seasons in California, a distinctive and pleasing vanilla-like fragrance derived from the leaves, stems and the flowers, the unusual ability to be propagated readily in a true prostrate form by cuttings, good resistance to insects and diseases, good weather tolerance, including good resistance to temperatures as high as 140° F. and as low as 18° F., good resistance to frost and/or occasional snow, and prolonged periods of drought (up to at least 8 months) and rainfall (up to as much as 9 to 14 inches) and the ability to thrive in heavy clay soils and in coastal salt wind conditions while growing in dredged ocean soils, as well as thriving in hot interior regions, with a pH tolerance as high as 9.6.

No reference cited

ROBERT E. BAGWILL, Primary Examiner